United States Patent
Lee et al.

(10) Patent No.: US 11,130,005 B2
(45) Date of Patent: Sep. 28, 2021

(54) COMPOSITION FOR IMPROVING SKIN AND PREVENTING HAIR-LOSS COMPRISING EXTRACELLULAR VESICLES FROM VEGETABLE EXTRACTION

(71) Applicant: PROSTEMICS CO. LTD., Seoul (KR)

(72) Inventors: Won Jong Lee, Seoul (KR); Eun Wook Choi, Seoul (KR); Su Kim, Seoul (KR); Eun Young Woo, Seoul (KR); Eun Joo Park, Seoul (KR); Ji Hyun Kim, Seoul (KR); Su Yeong Jeong, Seoul (KR)

(73) Assignee: Prostemics Co. Ltd.

( * ) Notice: Subject to any disclaimer, the term of this patent is extended or adjusted under 35 U.S.C. 154(b) by 0 days.

(21) Appl. No.: 15/762,948

(22) PCT Filed: Sep. 23, 2016

(86) PCT No.: PCT/KR2016/010658
§ 371 (c)(1),
(2) Date: Mar. 23, 2018

(87) PCT Pub. No.: WO2017/052267
PCT Pub. Date: Mar. 30, 2017

(65) Prior Publication Data
US 2018/0271773 A1 Sep. 27, 2018

(30) Foreign Application Priority Data
Sep. 25, 2015 (KR) ........................ 10-2015-0136901

(51) Int. Cl.
| | |
|---|---|
| *A61Q 7/00* | (2006.01) |
| *A61Q 19/02* | (2006.01) |
| *A61K 36/48* | (2006.01) |
| *A61Q 19/08* | (2006.01) |
| *A61K 36/899* | (2006.01) |
| *A61K 8/9794* | (2017.01) |
| *A61K 8/9789* | (2017.01) |
| *A61K 8/14* | (2006.01) |

(52) U.S. Cl.
CPC .................. *A61Q 7/00* (2013.01); *A61K 8/14* (2013.01); *A61K 8/9789* (2017.08); *A61K 8/9794* (2017.08); *A61K 36/48* (2013.01); *A61K 36/899* (2013.01); *A61Q 19/02* (2013.01); *A61Q 19/08* (2013.01)

(58) Field of Classification Search
CPC ............ A61K 8/14; A61K 8/97; A61Q 7/00
See application file for complete search history.

(56) References Cited

U.S. PATENT DOCUMENTS

| | | | | |
|---|---|---|---|---|
| 2012/0040003 A1* | 2/2012 | Yarovoy | .............. | A61K 8/4933 424/489 |
| 2014/0308212 A1 | 10/2014 | Zhang | | |
| 2016/0045448 A1* | 2/2016 | Zhang | .................. | A61K 31/519 514/249 |

FOREIGN PATENT DOCUMENTS

| | | | | | |
|---|---|---|---|---|---|
| DE | | 3120703 A1 * | 12/1982 | .............. | A61K 8/97 |
| DE | | 3332055 A1 * | 3/1985 | ............. | A61K 8/922 |
| JP | | S57-145804 | 9/1982 | | |
| JP | | 2003-313113 | 11/2003 | | |
| KR | | 10-1998-0000458 | 3/1998 | | |
| KR | | 10-2011-0038575 | 4/2011 | | |
| KR | | 10-2011-0082481 | 7/2011 | | |
| KR | | 10-2014-0006418 | 1/2014 | | |
| WO | | WO 2006/073181 | 7/2006 | | |
| WO | | WO 2014/159662 | 10/2014 | | |

OTHER PUBLICATIONS

DE-3332055-A1, Espacenet English translation, downloaded Jun. 2019 (Year: 2019).*
DE-3120703-A1, Espacenet English Translation, downloaded Oct. 2019 (Year: 2019).*
Shaffranthul et al (Indian Journal of Dermatology, 2007, vol. 52, p. 116) (Year: 2007).*
Hirata et al (Biol Pharm Bull, 2007, vol. 30, pp. 2402-2405) (Year: 2007).*
Perkins (Naturally Curly, The Benefits of Dragon Fruit Juice for Hair, Jul. 2015, https://www.naturallycurly.com/curlreading/home/the-benefits-of-dragon-fruit-for-hair-si) (Year: 2015).*
Viva Woman (https://www.vivawoman.net/2015/08/beauty-benefits-of-asparagus/, 2016 based on replies to blog post) (Year: 2016).*
CABI (Vigna unguiculata data sheet, Nov. 2019, https://www.cabi.org/isc/datasheet/56377) (Year: 2019).*
International Search Report prepared by the Korean Intellectual Property Office dated Dec. 27, 2016, for International Application No. PCT/KR2016/010658.
Mu et al. "Interspecies Communication between Plant and Mouse Gut Host Cells through Edible Plant Derived Exosome-like Nanoparticles," Molecular Nutrition & Food Research, Jul. 2014, vol. 58, No. 7, pp. 1561-1573.
Wang et al. "Targeted Drug Delivery to Intestinal Macrophages by Bioactive Nanovesicles Released from Grapefruit," Molecular Therapy, Mar. 2014, vol. 22, No. 3, pp. 522-534.
Castangia et al. "Fabrication of quercetin and curcumin bionanovesicles for the prevention and rapid regeneration of full-thickness skin defects on mice," Acta Biomaterialia, 2014, vol. 10, pp. 1292-1300.
Moulaoui et al. "Identification and nanoentrapment of polyphenolic phytocomplex from Fraxinus angustifolia: In vitro and in vivo wound healing potential," European Journal of Medicinal Chemistry, 2015, vol. 89, pp. 179-188.

* cited by examiner

*Primary Examiner* — Mark V Stevens
(74) *Attorney, Agent, or Firm* — Sheridan Ross P.C.

(57) ABSTRACT

The present invention relates to a composition containing extracellular vesicles derived from plant juice, wherein the extracellular vesicles have excellent skin condition-improving effects such as skin whitening, moisturizing and wrinkle reducing effects and exhibits an excellent effect of preventing hair loss by promotion of hair growth and regrowth, and the like.

3 Claims, 13 Drawing Sheets

COMPOSITION FOR IMPROVING SKIN AND PREVENTING HAIR-LOSS COMPRISING EXTRACELLULAR VESICLES FROM VEGETABLE EXTRACTION

CROSS REFERENCE TO RELATED APPLICATIONS

This application is a national stage application under 35 U.S.C. 371 and claims the benefit of PCT Application No. PCT/KR2016/010658 having an international filing date of 23 Sep. 2016, which designated the United States, which PCT application claimed the benefit of Korean Patent Application No. 10-2015-0136901 filed 25 Sep. 2015, the disclosure of each of which are incorporated herein by reference.

TECHNICAL FIELD

The present invention relates to a composition containing extracellular vesicles derived from plant juice, wherein the extracellular vesicles have excellent skin condition-improving effects such as skin whitening, moisturizing and wrinkle reducing effects and exhibits an excellent effect of preventing hair loss by promotion of hair growth and regrowth, and the like.

BACKGROUND ART

With recent improvements in medical technology and public health benefits, a super-aged society has been rapidly coming. Accordingly, improving the quality of life has been emphasized and the desire to maintain youth also increased. In order to delay and prevent aging that is the first to appear in the overall appearance, particularly the skin, many studies have been conducted in various regions.

Meanwhile, wrinkles are caused by aging of the skin, and skin aging results from the natural changes associated with the process of aging. Skin aging is broadly classified into two categories: physiological aging showing age-related changes in the skin function, structure or shape throughout the skin surface; and photo-aging caused by UV rays.

As skin aging progresses, changes in the dermis appear, and dermal atrophy appearing in people 70 years or older is a typical aging phenomenon. Changes in the dermis result from the changes in high-molecular-weight substances in the extracellular matrix due to decreases in the number of fibroblasts and the ability to form these fibroblasts. Specific examples of these changes include separation of collagen bundles, a decrease in mucopolysaccharide synthesis, decreases in the number and diameter of collagen and elastin, decomposition of collagen and elastin, blood vessel expansion, and the like. Generally, among various factors, including the skin's moisture content, collagen content and immune responses to external environments, the expression level and activity of collagenase, a collagen-degrading enzyme that reduces the production and content of collagen, have the greatest effect on the formation of wrinkles.

The human skin color is determined according to the concentration and distribution of melanin in the skin. The melanin pigment that is produced in the melanocytes of the human skin is a phenolic polymer consisting of a complex of a black pigment and a protein and plays an important role in preventing skin damage from being caused by UV rays. The activity of tyrosinase present in melanocytes was reported to be the most important factor in melanin biosynthesis, and tyrosinase plays an important role in the skin darkening process by converting tyrosine, which is a kind of amino acid, into DOPA and dopaquinone, which are intermediate products of melanin polymer production.

Meanwhile, the imbalance of hormones is becoming more severe due to environmental pollution, automobile exhaust gases and the like. For this reason, the rate of hair loss increases, the age of people having hair loss decreases, and the skin immune system is affected, thus causing various skin diseases such as atopy or psoriasis. In addition, due to a change in eating habits toward instant foods and meats, people suffering from obesity are increasing rapidly, despite their young age.

Thus, in-depth studies have been conducted to develop substances which can effectively solve various phenomena, for example, formation of wrinkles by intrinsic aging and UV rays, discolorations or freckles, obesity, immune imbalance, and hair loss, which are disadvantageous in aesthetic terms and also become serious social problems.

DISCLOSURE

Technical Problem

It is an object of the present invention to provide a composition for improving skin conditions, which is safe and has excellent effects on skin moisturization, skin whitening, wrinkle reduction, anti-aging and the like.

Another object of the present invention is to provide a composition which is safe and has excellent effects on wound healing or the promotion of wound healing.

Still another object of the present invention is to provide a composition which is safe and can prevent or treat hair loss due to its excellent effect on the promotion of hair growth and regrowth.

Technical Solution

The skin is composed of epidermis, dermis and subcutaneous tissue. The epidermis that is the skin's outer layer is composed of stratified squamous epithelium and acts as a barrier that protects the body against external environments. The epidermis is composed of five layers; from outer to inner, they are the stratum corneum, stratum lucidum, stratum granulosum, stratum spinosum, and stratum basale. The dermis is a layer between the epidermis and the subcutaneous tissue, is composed of papillary dermis and reticular dermis, and includes blood vessels, collagen, elastin fiber, pores, arrector pili muscles, sebaceous gland, sweat gland, various sensory nerves, fibroblasts, macrophages and the like, which are not present in the epidermis. The dermis makes up the largest portion of the skin.

The dermis is composed mainly of collagen and elastin fibers which serve to support the skin. For this reason, when problems occur in this dermis, wrinkles are formed and skin elasticity is lost, and thus skin aging progresses. Collagen is known to play an important role in skin regeneration, skin moisture content, wound healing, wrinkle reduction, and the like, and is produced by fibroblasts. Collagen has the capability to contain a large amount of moisture, and thus functions to provide moisture to the dermis. As skin aging progresses, the capability of collagen to contain moisture decreases, and thus wrinkles increase. In addition, when a wound is created, collagen also acts to heal the wound by filling in the wound through the continuous production of collagen by fibroblasts.

In addition, in the modern society, a living body is gradually damaged due to a lot of stress, and hair loss caused by this stress becomes a big social issue. Hair loss is caused by a variety of factors, including poor hair growth and lack of growth factors that promote hair follicle cell growth.

Such hair loss reduces the quality of life due to mental stress and significantly affects interpersonal relations or social life.

In the social life, the image from the appearance is very impressive, and the importance of the appearance is the invisible power of self-esteem or social life. For this reason, interest in the causes and treatment of hair loss is increasing day by day.

The present inventors have found that extracellular vesicles derived from plant juice have an excellent ability to penetrate the skin, exhibit excellent effects on wound healing, skin moisturization, skin whitening, wrinkle reduction, anti-aging and the like when absorbed into the skin, and also have excellent effects on the promotion of hair growth and regrowth, thereby reaching the present invention.

In accordance with one embodiment of the present invention, there is provided a cosmetic composition for improving skin conditions, which contains, as an active ingredient, extracellular vesicles derived from plant juice. More preferably, the extracellular vesicles may be contained at a concentration of 5 to 10 μg/ml.

In the present invention, the plant juice is preferably a juice obtained by extracting a plant using a screw having a stirring speed of 20 to 100 rpm, because this juice contains a large amount of extracellular vesicles having an excellent effect of improving skin conditions.

In accordance with another embodiment of the present invention, there is provided a food composition for improving skin conditions, which contains, as an active ingredient, extracellular vesicles derived from plant juice. More preferably, the extracellular vesicles may be contained at a concentration of 5 to 10 μg/ml.

In the present invention, the plant juice is preferably a juice obtained by extracting a plant using a screw having a stirring speed of 20 to 100 rpm, because this juice contains a large amount of extracellular vesicles having an excellent effect of improving skin conditions.

In accordance with still another embodiment of the present invention, there is provided a pharmaceutical composition for wound healing, which contains, as an active ingredient, extracellular vesicles derived from plant juice. More preferably, the extracellular vesicles may be contained at a concentration of 5 to 10 μg/ml.

In the present invention, the plant juice is preferably a juice obtained by extracting a plant using a screw having a stirring speed of 20 to 100 rpm, because this juice contains a large amount of extracellular vesicles having an excellent wound healing effect.

In accordance with still another embodiment of the present invention, there is provided a pharmaceutical composition for preventing or treating hair loss, which contains, as an active ingredient, extracellular vesicles derived from plant juice. More preferably, the extracellular vesicles may be contained at a concentration of 5 to 10 μg/ml.

In the present invention, the plant juice is preferably a juice obtained by extracting a plant using a screw having a stirring speed of 20 to 100 rpm, because this juice contains a large amount of extracellular vesicles having an excellent effect of promoting hair growth and regrowth.

In accordance with still another embodiment of the present invention, there is provided a cosmetic composition for reducing hair loss, which contains, as an active ingredient, extracellular vesicles derived from a plant. More preferably, the extracellular vesicles may be contained at a concentration of 5 to 10 μg/ml.

In the present invention, the plant juice is preferably a juice obtained by extracting a plant using a screw having a stirring speed of 20 to 100 rpm, because this juice contains a large amount of extracellular vesicles having an excellent effect of promoting hair growth and regrowth.

In accordance with still another embodiment of the present invention, there is provided a food composition for reducing hair loss, which contains, as an active ingredient, extracellular vesicles derived from a plant. More preferably, the extracellular vesicles may be contained at a concentration of 5 to 10 μg/ml.

In the present invention, the plant juice is preferably a juice obtained by extracting a plant using a screw having a stirring speed of 20 to 100 rpm, because this juice contains a large amount of extracellular vesicles having an excellent effect of promoting hair growth and regrowth.

In accordance with still another embodiment of the present invention, there is provided a method for preparing a cosmetic or food composition for improving skin conditions, the method comprising the steps of:

obtaining a plant juice by extracting a plant using a screw;

subjecting the plant juice to static incubation;

centrifuging the incubated plant juice and collecting a supernatant; and filtering the supernatant through a filter membrane including pores having an average pore size of 0.1 to 1.0 μm, and collecting a filtrate.

The filtrate obtained through the above-described process in the present invention contains a large amount of extracellular vesicles, has an excellent ability to penetrate the skin, and exhibits excellent effects on wound healing, skin moisturization, skin whitening, wrinkle reduction, anti-aging and the like when absorbed into the skin.

In the present invention, before the plant is extracted, a step of washing the plant to remove impurities may additionally be performed, if necessary.

Furthermore, the screw that is used in the present invention is preferably a low-speed screw having a stirring speed of 20 to 100 rpm, because this screw makes it possible to obtain a plant juice containing a large amount of extracellular vesicles having an excellent effect of improving skin conditions.

Furthermore, in the present invention, the static incubation may be performed at a temperature of 20 to 30° C. for 12 to 48 hours.

Furthermore, in the present invention, the centrifuging may be performed one time or more at 100 to 20,000 g for 10 to 120 minutes.

Furthermore, in the present invention, the centrifuging may be performed at 100 to 500 g for 10 to 30 minutes for first centrifugation, and then performed at 1,000 to 2,000 g for 10 to 30 minutes for second centrifugation, and then performed at 5,000 to 20,000 g for 30 minutes to 1 hour for third centrifugation.

Furthermore, in the present invention, the filtering may be performed one time or more using a filtration membrane including pores having an average pore size of 0.2 to 0.5 μm. Preferably, the filtering may be performed using a filtration membrane including pores having an average pore size of 0.4 to 0.5 μm for first filtration, and then performed using a filtration membrane including pores having an average pore size of 0.2 to 0.3 μm for second filtration. In this case, it is possible to obtain a filtrate containing a large amount of extracellular vesicles having an excellent effect of improving skin conditions.

In accordance with still another embodiment of the present invention, there is provided a method for preparing a pharmaceutical composition for wound healing or wound healing promotion, the method comprising the steps of:

obtaining a plant juice by extracting a plant using a screw;

subjecting the plant juice to static incubation;

centrifuging the incubated plant juice and collecting a supernatant; and filtering the supernatant through a filter membrane including pores having an average pore size of 0.1 to 1.0 µm, and collecting a filtrate.

The filtrate obtained through the above-described process in the present invention contains a large amount of extracellular vesicles, is safe, and also has excellent effects on wound healing or promotion of wound healing.

In the present invention, before the plant is extracted, a step of washing the plant to remove impurities may additionally be performed, if necessary.

Furthermore, the screw that is used in the present invention is preferably a low-speed screw having a stirring speed of 20 to 100 rpm, because this screw makes it possible to obtain a plant juice containing a large amount of extracellular vesicles having an excellent wound healing effect.

Furthermore, in the present invention, the static incubation may be performed at a temperature of 20 to 30° C. for 12 to 48 hours.

Furthermore, in the present invention, the centrifuging may be performed one time or more at 100 to 20,000 g for 10 to 120 minutes.

Furthermore, in the present invention, the centrifuging may be performed at 100 to 500 g for 10 to 30 minutes for first centrifugation, and then performed at 1,000 to 2,000 g for 10 to 30 minutes for second centrifugation, and then performed at 5,000 to 20,000 g for 30 minutes to 1 hour for third centrifugation.

Furthermore, in the present invention, the filtering may be performed one time or more using a filtration membrane including pores having an average pore size of 0.2 to 0.5 µm. Preferably, the filtering may be performed using a filtration membrane including pores having an average pore size of 0.4 to 0.5 µm for first filtration, and then performed using a filtration membrane including pores having an average pore size of 0.2 to 0.3 µm for second filtration. In this case, it is possible to obtain a filtrate containing a large amount of extracellular vesicles having an excellent would-healing effect.

In accordance with still another embodiment of the present invention, there is provided a method for preparing a pharmaceutical, cosmetic or food composition for preventing, reducing or treating hair loss, the method comprising the steps of:

obtaining a plant juice by extracting a plant using a screw;

subjecting the plant juice to static incubation;

centrifuging the incubated plant juice and collecting a supernatant; and filtering the supernatant through a filter membrane including pores having an average pore size of 0.1 to 1.0 µm, and collecting a filtrate.

The filtrate obtained through the above-described process in the present invention contains a large amount of extracellular vesicles, is safe, and also has excellent effects on the promotion of hair growth and regrowth.

In the present invention, before the plant is extracted, a step of washing the plant to remove impurities may additionally be performed, if necessary.

Furthermore, the screw that is used in the present invention is preferably a low-speed screw having a stirring speed of 20 to 100 rpm, because this screw makes it possible to obtain a plant juice containing a large amount of extracellular vesicles having an excellent effect of promoting hair growth and regrowth.

Furthermore, in the present invention, the static incubation may be performed at a temperature of 20 to 30° C. for 12 to 48 hours.

Furthermore, in the present invention, the centrifuging may be performed one time or more at 100 to 20,000 g for 10 to 120 minutes.

Furthermore, in the present invention, the centrifuging may be performed at 100 to 500 g for 10 to 30 minutes for first centrifugation, and then performed at 1,000 to 2,000 g for 10 to 30 minutes for second centrifugation, and then performed at 5,000 to 20,000 g for 30 minutes to 1 hour for third centrifugation.

Furthermore, in the present invention, the filtering may be performed one time or more using a filtration membrane including pores having an average pore size of 0.2 to 0.5 µm. Preferably, the filtering may be performed using a filtration membrane including pores having an average pore size of 0.4 to 0.5 µm for first filtration, and then performed using a filtration membrane including pores having an average pore size of 0.2 to 0.3 µm for second filtration. In this case, it is possible to obtain a filtrate containing a large amount of extracellular vesicles having an excellent effect of promoting hair growth and regrowth.

As used herein, the term "extracellular vesicles" refers to membranous sacs secreted from various cells and is also defined as nanovesicles. The extracellular vesicles have a diameter of about 30 to 1,000 nm, and preferably have an average diameter of 100 to 300 nm, and mean sacs that are released extracellularly when the fusion between multivesicular bodies and plasma membranes occurs.

As used herein, the term "plant" is understood to mean not only mature plants, but also plant cells, plant tissues and plant's seeds, which may develop into mature plants.

Although the kind of plant that may be used in the present invention is not particularly limited, the plant may be, for example, a plant selected from the group consisting of food crops, including rice, wheat, barley, corn, bean, potato, red bean, oats and sorghum; vegetable crops, including *Arabidopsis*, Chinese cabbage, radish, pepper, garlic, ginger, strawbeny, tomato, watermelon, cucumber, cabbage, oriental melon, pumpkin, Welsh onion, onion, asparagus and carrot; special crops, including ginseng, tobacco, cotton, sesame, sugar cane, sugar beet, perilla, peanut, and rape; fruit trees, including an apple tree, a pear tree, a jujube tree, a peach tree, a kiwi fruit tree, a grape tree, a citrus fruit tree, a persimmon tree, an orange tree, a grapefruit tree, a plum tree, an apricot tree, a dragon fruit tree, a mango tree, a blueberry tree, an avocado tree, and a banana tree; flowers, including rose, gladiolus, gerbera, carnation, chrysanthemum, lily, and tulip; and fodder crops, including ryegrass, red clover, orchard grass, alfalfa, tall fescue, and perennial ryegrass. However, the kind of plant that may be used in the present invention is not limited to the above-listed kinds, and any plant may be used without limitations, as long as it belongs to plant species.

As used herein, the term "plant juice" means a liquid fluid obtained by extracting water and the like from a plant by a mechanical force or torque. Examples of the plant juice include, but are not limited to, fruit juice, vegetable juice, plant juice, and the like.

In addition, the pharmaceutical composition of the present invention may further contain suitable carriers, excipients or diluents according to a conventional method. Carriers, excipients and diluents, which may be contained in the pharmaceutical composition of the present invention, include, but are not limited to, lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinylpyrrolidone, methylhydroxy benzoate, propylhydroxy benzoate, talc, magnesium stearate, mineral oils, and the like.

For use, the pharmaceutical composition according to the present invention may be formulated as oral dosage forms, including powders, granules, tablets, capsules, suspensions, emulsions, syrups, aerosols and the like, external preparations, suppositories or sterile injectable solutions, according to conventional methods. Specifically, the pharmaceutical composition of the present invention may be formulated with diluents or excipients, such as fillers, extenders, binders, wetting agents, disintegrants, surfactants, etc., which are commonly used. Solid formulations for oral administration include tablets, pills, powders, granules, capsules and the like, and such solid formulations may be prepared by mixing the pharmaceutical composition of the present invention with at least one excipient, for example, starch, calcium carbonate, sucrose, lactose, gelatin or the like. In addition to simple excipients, lubricants such as magnesium stearate or talc may also be used. Liquid formulations for oral administration include suspensions, solutions, emulsions, syrup and the like, and may contain various excipients, for example, wetting agents, flavoring agents, aromatics, preservatives and the like, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like may be used. As the base of the suppositories, witepsol, Macrogol, Tween 61, cacao butter, laurin fat, glycerogelatin and the like may be used.

Routes for administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal intrarectal, local, sublingual or intrarectal routes. Oral or parenteral administration is preferred. As used herein, the term "parenteral" is meant to include subcutaneous, intradermal, intravenous, intramuscular, intra-articular, intrabursal, intrastemal, intrathecal, intralesional and intracranial injection or infusion techniques. The pharmaceutical composition of the present invention may also be administered in the form of suppositories for rectal administration.

The dose of the pharmaceutical composition of the present invention may vary depending on various factors, including the activity of a particular compound used, the patient's age, body weight, general health, sex, diet, administration time, the route of administration, excretion rate, drug combination, and the severity of a particular disease to be prevented or treated, and can be suitably determined by a person skilled in the art depending on the patient's condition, body weight, the severity of the disease, the form of drug, the route of administration, and the period of administration. The pharmaceutical composition of the present invention may be administered at a dose of 0.0001-50 mg/kg/day or 0.001-50 mg/kg/day. The pharmaceutical composition of the present invention may be administered once or several times a day. The dose does not limit the scope of the present invention in any way. The pharmaceutical composition according to the present invention may be formulated as pills, sugar-coated tablets, capsules, liquids, gels, syrups, slurries, or suspensions.

The food composition of the present invention may be prepared as various foods, for example, beverages, gums, teas, vitamin complexes, powders, granules, tablets, capsules, confectionery, cakes, bread and the like. The food composition of the present invention is based on a plant extract having little or no toxicity and side effects, and thus may be used without anxiety for preventive purposes over a long period of time.

When either extracellular vesicles derived from plant juice or a filtrate containing the same is contained as an active ingredient in a food composition according to the present invention, it may be added in an amount of 0.1 to 50 wt % based on the total weight of the composition.

When the food composition is prepared as a beverage, there is no particular limitation, except that the beverage contains the food composition at the indicated percentage. The beverage may additionally contain various flavorings or natural carbohydrates, like conventional beverages. Examples of the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, stevia extracts, such as rebaudioside A, glycyrrhizin, etc.) and synthetic flavorings (saccharin, aspartame, etc.).

In addition, the food composition of the present invention may contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents as used in carbonated beverages, etc. Such components may be used individually or in combination. Although the percentage of such additives is not of great importance, it is generally selected in the range of 0.1 to about 50 parts by weight based on 100 parts by weight of the food composition of the present invention.

In addition, the cosmetic composition of the present invention may be prepared as skin softeners, nourishing lotions, nourishing essences, massage creams, cosmetic bath water additives, body lotions, body milks, bath oils, baby oils, baby powders, shower gels, shower creams, sun screen lotions, sun screen creams, suntan creams, skin lotions, skin creams, UV blocking cosmetics, cleansing milks, hair removing agents (for cosmetic purposes), face and body lotions, face and body creams, skin whitening creams, hand lotions, hair lotions, cosmetic creams, Jasmine oils, bath soaps, liquid soaps, cosmetic soaps, shampoos, hand cleaners, medicinal soaps (for non-medical purposes), cream soaps, facial washes, systemic cleansers, scalp cleansers, hair rinses, toilet soaps, tooth whitening gels, toothpastes, and the like. To this end, the composition of the present invention may further contain either a solvent which is conventionally used in the preparation of cosmetic compositions, or a suitable carrier, excipient or diluent.

Although the kind of solvent that may further be added to the cosmetic composition of the present invention is not particularly limited, the solvent may be, for example, water, saline, DMSO, or combinations thereof. In addition, carriers, excipients or diluents, which may be used in the present invention, include, but are not limited to, purified water, oils, waxes, fatty acids, fatty acid alcohols, fatty acid esters, surfactants, humectants, thickeners, antioxidants, viscosity stabilizers, chelating agents, buffers, lower alcohols and the like. In addition, the cosmetic composition of the present invention may, if necessary, contain whitening agents, moisturizing agents, vitamins, UV blocking agents, fragrances, dyes, antibiotics, antibacterial agents, or antifungal agents.

The oils that may be used in the present invention include hydrogenated vegetable oils, castor oil, cottonseed oil, olive oil, palm oil, jojoba oil, and avocado oil, and the waxes that may be used in the present invention include beeswax, spermaceti wax, carnauba wax, candelilla wax, montan wax, ceresin wax, liquid paraffin, and lanolin.

The fatty acids that may be used in the present invention include stearic acid, linoleic acid, linolenic acid, and oleic acid, and the fatty acid alcohols that may be used in the present invention include cetyl alcohol, octyl dodecanol, oleyl alcohol, panthenol, lanolin alcohol, stearyl alcohol, and hexadecanol, and the fatty acid esters that may be used in the present invention include isopropyl myristate, isopropyl palmitate, and butyl stearate. The surfactants that may be used in the present invention include cationic surfactants, anionic surfactants and nonionic surfactants, which are known in the art. Among these surfactants, surfactants of natural origin are preferred.

In addition, the cosmetic composition of the present invention may contain humectants, thickeners, antioxidants and the like, which are widely known in the art, and the kinds and amounts of these components are as known in the art.

Advantageous Effects

The plant-derived extracellular vesicles which are provided according to the present invention have an excellent ability to penetrate the skin, exhibit excellent skin condition-improving effects such as skin moisturization, skin whitening, wrinkle reduction and anti-aging when absorbed into the skin, cause no irritation or side effects on the skin, and are safe.

Furthermore, the plant-derived extracellular vesicles which are provided according to the present invention promote cell proliferation in wound sites, and increase the expression levels of growth factors and the like that have excellent wound healing effects, indicating that these extracellular vesicles have excellent wound healing activity or wound healing promotion activity.

In addition, the plant-derived extracellular vesicles which are provided according to the present invention have an excellent effect of preventing and treating hair loss by promoting hair growth and regrowth, and are safe without side effects even when they are taken or applied to the skin.

BEST MODE

Figure 1:
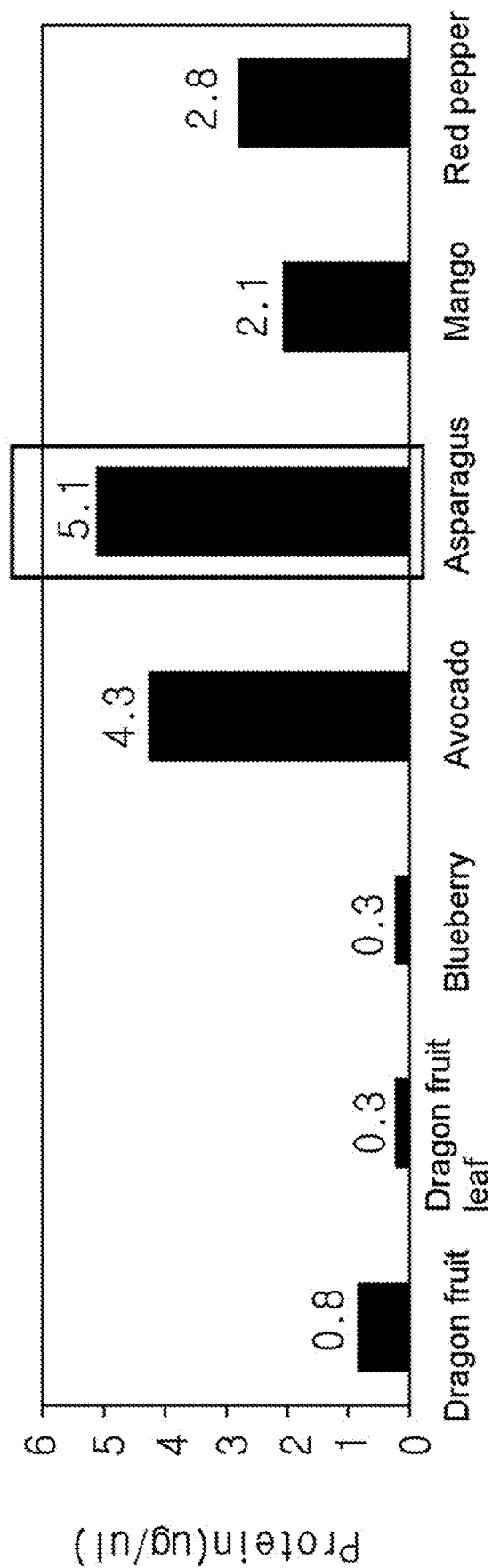
FIG. 1 shows the results of measuring the content of protein in a filtrate obtained from each of dragon fruit, dragon fruit leaf, blueberry, avocado, asparagus, mango and pepper in Experimental Example 1.

In accordance with one embodiment of the present invention, there is provided a cosmetic composition for improving skin conditions, which contains, as an active ingredient, extracellular vesicles derived from plant juice. Moore preferably, the extracellular vesicles may be contained at a concentration of 5 to 10 µg/ml.

In accordance with another embodiment of the present invention, there is provided a food composition for improving skin conditions, which contains, as an active ingredient, extracellular vesicles derived from plant juice.

In accordance with still another embodiment of the present invention, there is provided a pharmaceutical composition for wound healing, which contains, as an active ingredient, extracellular vesicles derived from plant juice.

In accordance with still another embodiment of the present invention, there is provided a pharmaceutical composition for preventing or treating hair loss, which contains, as an active ingredient, extracellular vesicles derived from plant juice.

In accordance with still another embodiment of the present invention, there is provided a cosmetic composition for reducing hair loss, which contains, as an active ingredient, extracellular vesicles derived from plant juice.

In accordance with still another embodiment of the present invention, there is provided a food composition for reducing hair loss, which contains, as an active ingredient, extracellular vesicles derived from plant juice.

Mode for Invention

Hereinafter, preferred embodiments of the present invention will be described. However, the present invention may be embodied in a variety of different forms, and the scope of the present invention is not limited to the embodiments described below. In addition, these embodiments are provided so that this disclosure will be thorough and complete, and will fully convey the scope of the present invention to those skilled in the art.

EXAMPLES

Example 1

Each of dragon fruit, dragon fruit leaf, blueberry, avocado, asparagus, mango, cowpea, pepper, pomegranate and turmeric was washed with distilled water, and then extracted using a low-speed screw having a stirring speed of 40 rpm. The resulting liquid plant juices were filtered through a sieve to remove floating matter. Next, the plant juices were incubated at 25° C. for 10 minutes and centrifuged at 2,000 g for 30 minutes. Each of the supernatants was isolated, filtered through a polyvinylidene difluoride filter membrane including 0.45 μm pores, and then filtered through a polyvinylidene difluoride filter membrane including 0.22 μm pores, thereby obtaining filtrates.

Experimental Example 1

In order to examine the content and distribution of extracellular vesicles in the filtrates obtained in Example 1 above, the content of protein in the filtrate obtained from each of dragon fruit, dragon fruit leaf, blueberry, avocado, asparagus, mango and pepper was measured using the Bradford protein assay. The results of the measurement are graphically shown in FIG. 1.

In addition, the size-dependent distribution and particle number of extracellular vesicles in a filtrate obtained from each of bean, garlic and ginger were measured by nanoparticle tracking analysis (NTA), and the results are shown in Table 1 below and FIG. 2. Furthermore, extracellular vesicles in the filtrate obtained from bean are imaged using a transmission electron microscope (TEM), and the images are shown in FIG. 3.

TABLE 1

| Material | Average size (nm) | Particles/ml |
|---|---|---|
| Bean | 154.8 | $4.7 \times 10^8$ |
| Garlic | 189.6 | $1.69 \times 10^8$ |
| Ginger | 122.5 | $2.91 \times 10^7$ |

As can be seen in FIG. 1, the filtrate obtained from each of dragon fruit, dragon fruit leaf, blueberry, avocado, asparagus, mango and pepper appears to contain a considerable amount of protein, that is, extracellular vesicles. In particular, it could be seen that the filtrate obtained from each of avocado and asparagus contained a large amount of protein.

Figure 2:
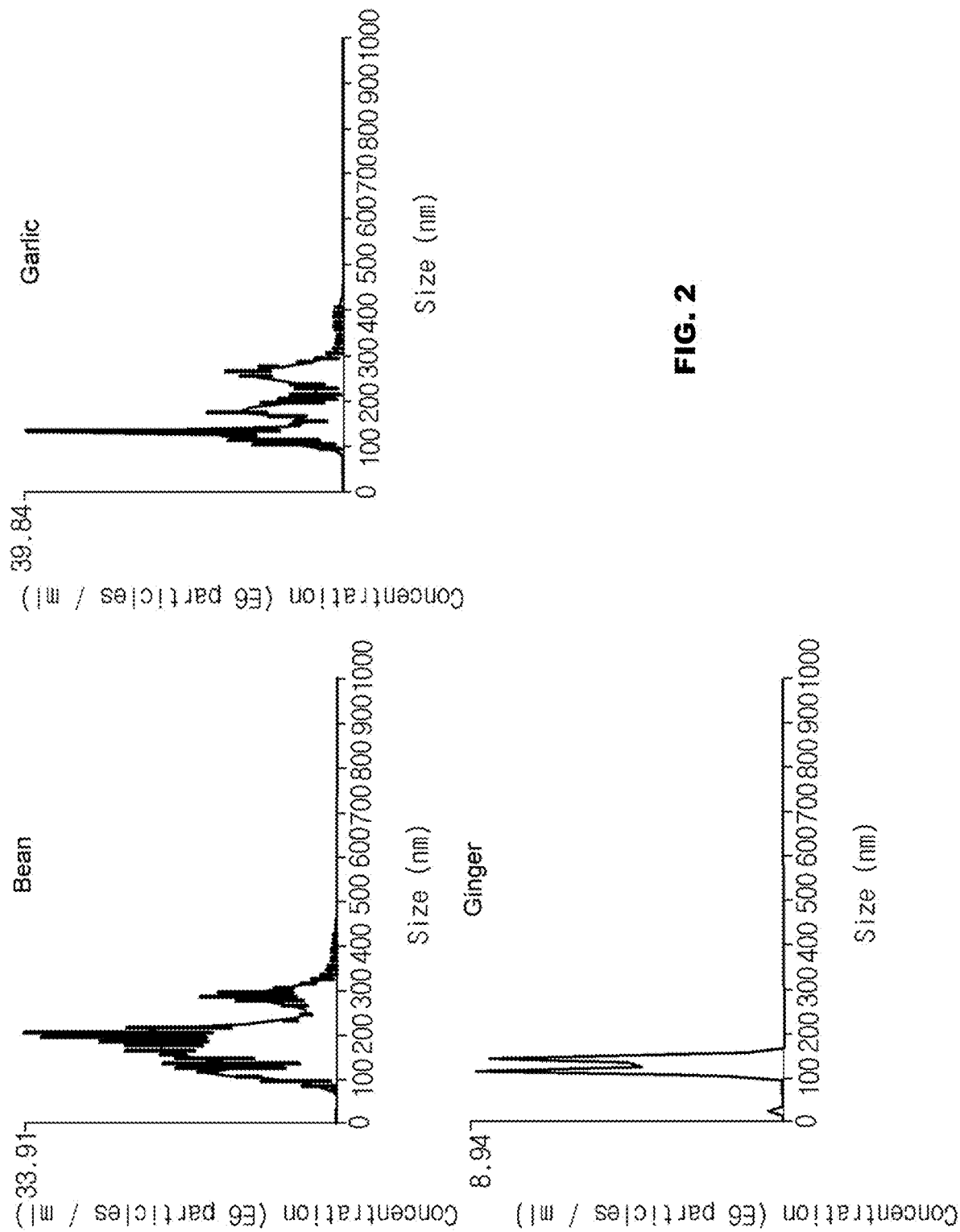
FIG. 2 shows the results of measuring the size-dependent concentration of particles in a filtrate obtained from each of bean, garlic and ginger in Experimental Example 1.
Figure 3:
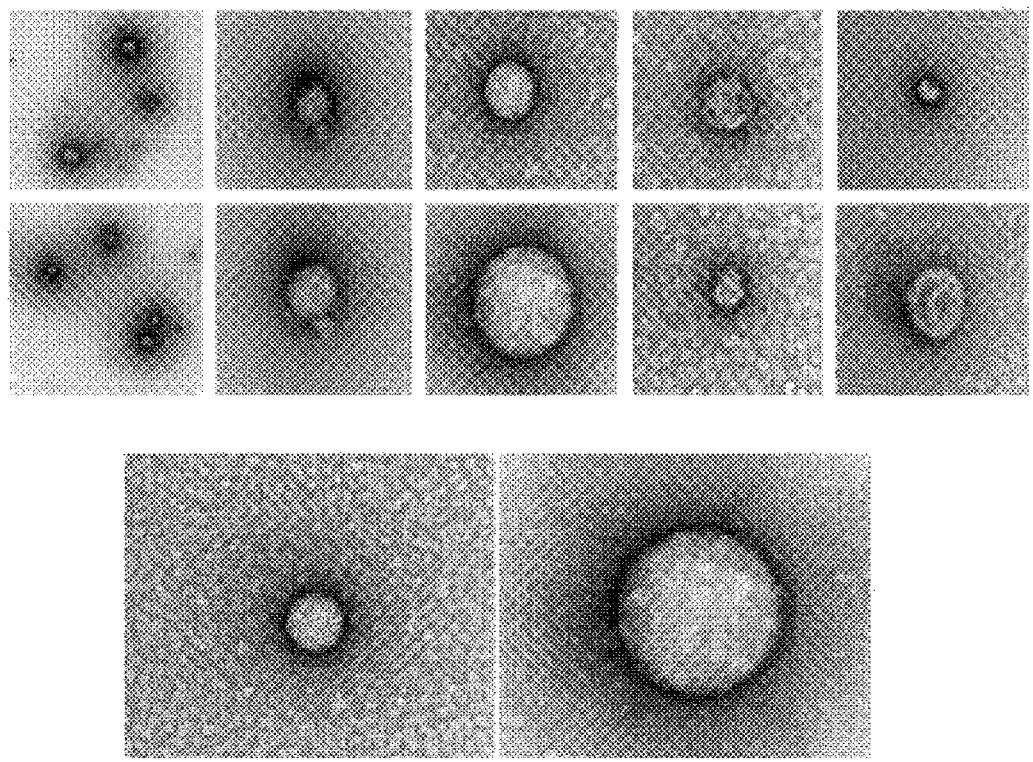
FIG. 3 shows transmission electron microscope (TEM) images of extracellular vesicles in a filtrate obtained from bean in Experimental Example 1.

Furthermore, as can be seen in FIG. 2 and Table 1 above, the average size of particles contained in the filtrate obtained from each of bean, garlic and ginger was 100 to 200 nm, and as can be seen from the transmission electron microscope images in FIG. 3, these particles had a spherical structure. This suggests that the particles contained in the filtrates obtained from the above-described plants are equivalent to extracellular vesicles.

Experimental Example 2

$2 \times 10^4$ fibroblasts/ml were seeded into a 24-well plate. After 24 hours, extracellular vesicles obtained from cowpea were labeled using a PKH26 red fluorescent cell linker kit (Sigma), and then the fibroblasts were treated with extracellular vesicles. After 6 hours of incubation, the fibroblasts were incubated with a dilution of 1 μm DAPI in PBS under a dark condition for 5 minutes, and washed with PBS. Then, the fibroblasts were imaged with a fluorescence microscope, and the results are shown in FIG. 4.

Figure 4:
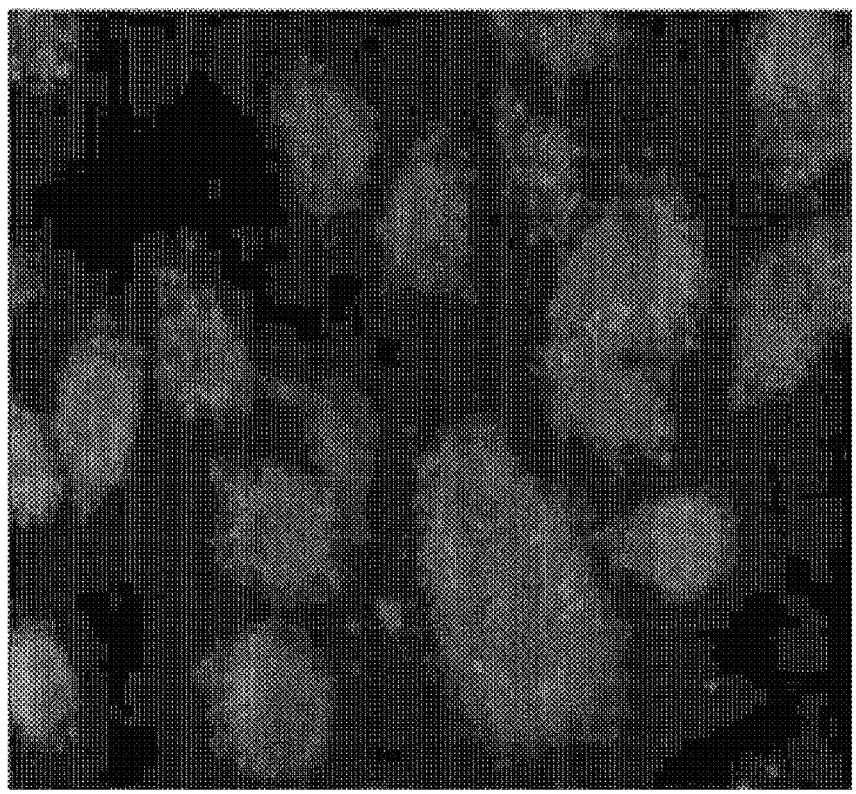
FIG. 4 is a fluorescence microscope image obtained in Experimental Example 2 and showing that labeled extracellular vesicles were absorbed into fibroblasts.

As can be seen in FIG. 4, the PKH26-labeled, plant-derived extracellular vesicles migrated into the cytoplasm of the fibroblasts.

This suggests that when the plant-derived extracellular vesicles according to the present invention are applied to the skin or the like, they can be easily absorbed into cells, thereby exhibiting excellent effects.

Experimental Example 3

$2 \times 10^4$ dermal papilla cells (DPCs)/ml were equally seeded into a 24-well plate (SPL, Korea). After 24 hours of stabilization, the cells were treated for 48 hours with the extracellular vesicle-containing filtrates obtained in Example 1. MTS reagent (Promega, USA) was diluted with cell basal medium (FBS-free, 1% p/s) at a ratio of 1:5, and 500 μl of the dilution was dispensed into each well of the plate and incubated for 1 hour and 30 minutes. Next, the absorbance at a wavelength of 490 nm was measured to evaluate changes in cell viability, and the results are graphically shown in FIG. 5. However, a positive control group was treated with 10% fetal bovine serum (FBS), and a negative control group was not treated with anything.

Figure 5:
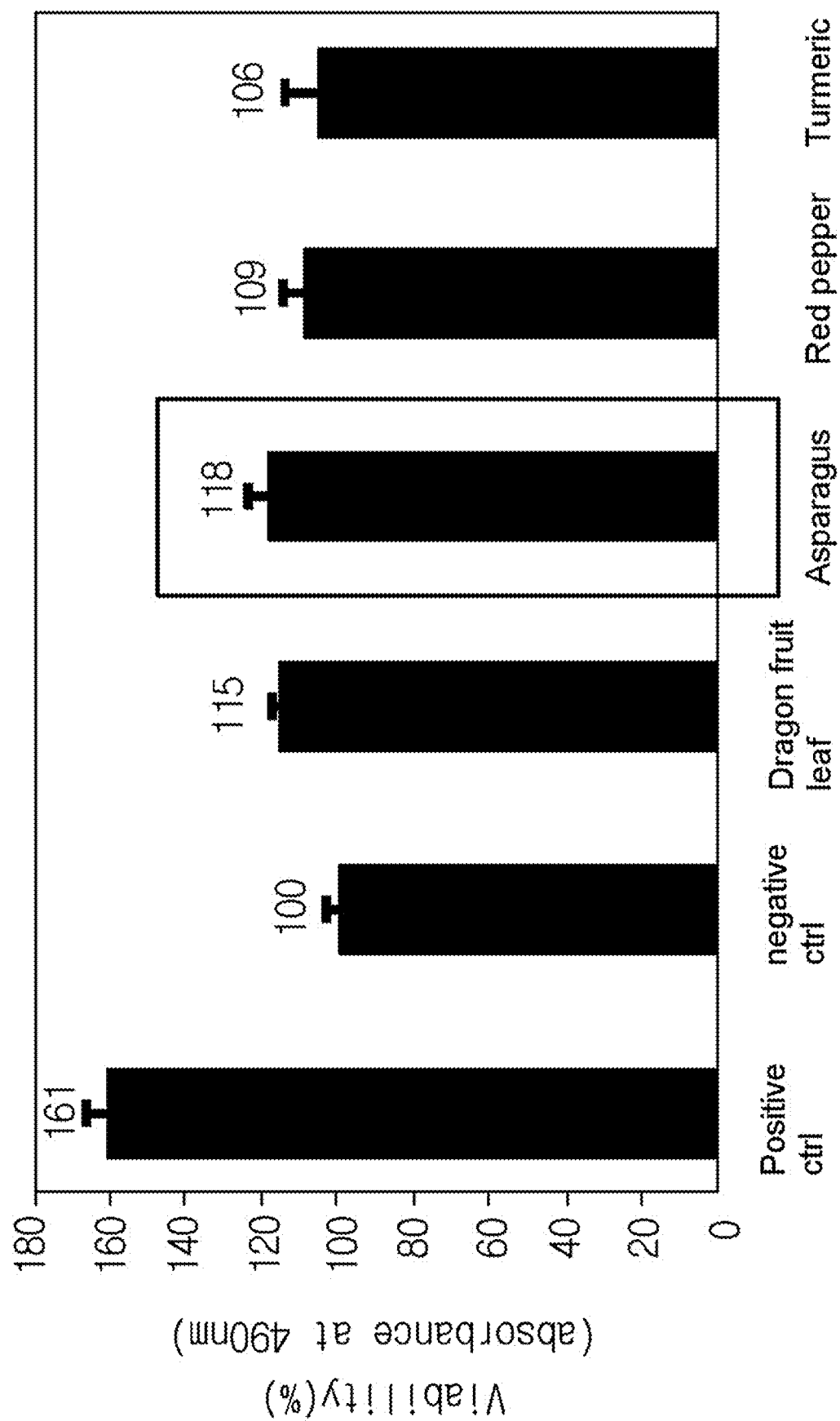
FIG. 5 shows the results of measuring changes in cell viability after treating dermal papilla cells with plant-derived extracellular vesicles in Experimental Example 3.

As can be seen in FIG. 5, when the cells were treated with the extracellular vesicles derived from each of dragon fruit leaf, asparagus, pepper and turmeric, the cell viability increased. In particular, it could be seen that when the cells were treated with the extracellular vesicles derived from asparagus, the cell viability significantly increased.

Experimental Example 4

$5 \times 10^5$ dermal papilla cells (DPCs)/ml were equally seeded into a 60 mm dish (SPL, Korea), and the cells were treated for 48 hours with the extracellular vesicle-containing filtrate obtained from bean in Example 1. Next, RNA was isolated from the cells by use of an RNA isolation kit (Quiagen, USA), and then primers for 1 μg of the isolated RNA were synthesized using a cDNA synthesis kit (Intronbio, Korea). The primers were used at a concentration of 10 pmol/μl. The expression levels of LEF-1 (lymphoid enhancer-binding factor-1), Versican, Gli-1 and Ptc-1 (the patched protein-1) genes were detected by adding 2×SYBR green master mix (Takara, Japan), and the results are graphically shown in FIG. 6. However, a control group was not treated with anything.

Figure 6:
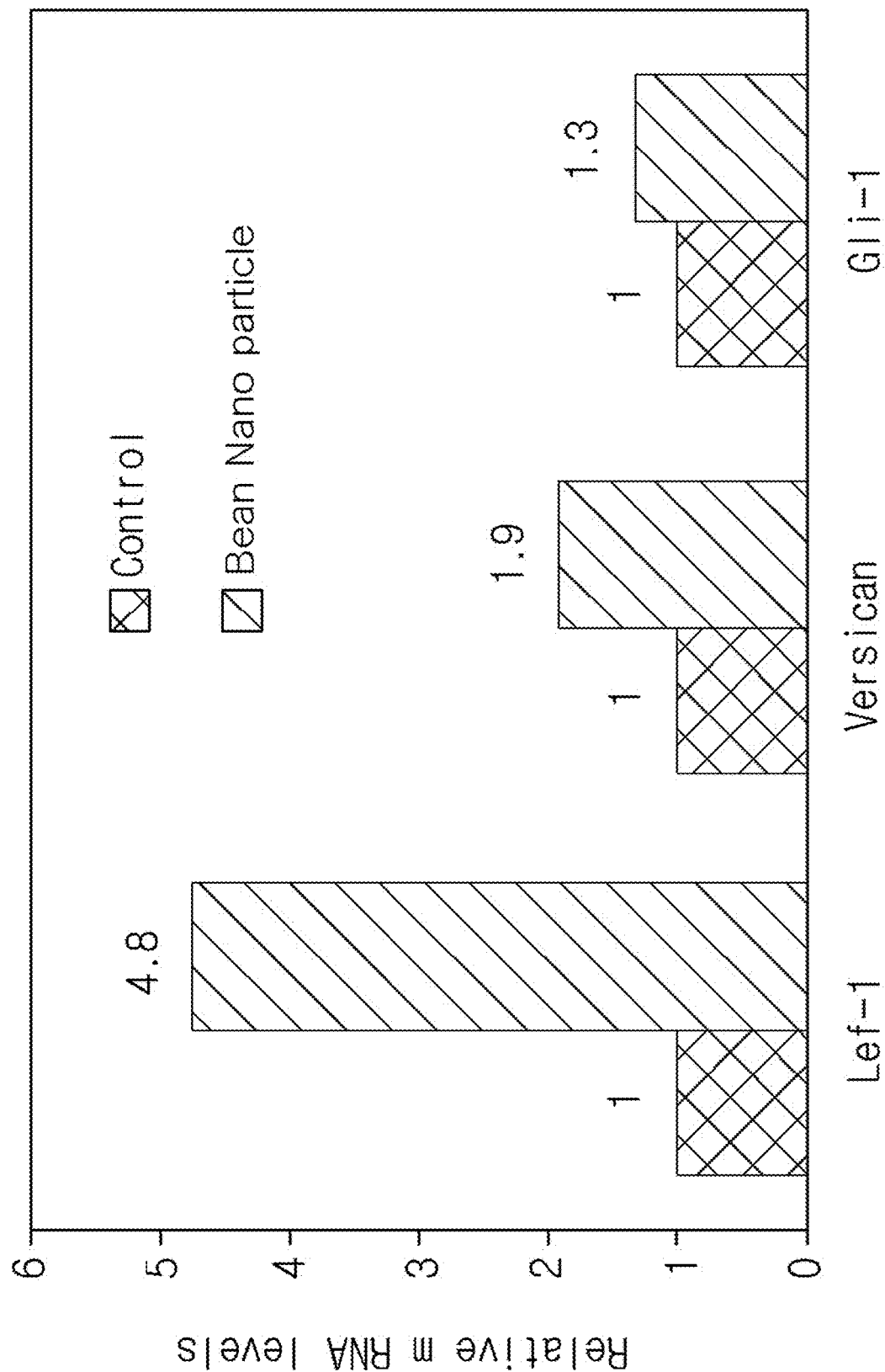
FIG. 6 shows the results of measuring the expression levels of Lef-1, Versican and Gli-1 genes after treating dermal papilla cells with bean-derived extracellular vesicles in Experimental Example 4.

As can be seen in FIG. 6, when the cells were treated with the bean-derived extracellular vesicles, the expression levels of Lef-1, Versican and Gli-1 genes increased. In this regard, the Lef-1 is a gene that promotes the formation and differentiation of hair follicles, the Versican is a gene involved in induction of hair follicle formation, hair regeneration, and maintenance of hair growth, and the Gli-1 is a gene that promotes hair follicle formation and hair growth.

As a result, the above-described results suggest that the plant-derived extracellular vesicles according to the present invention have an excellent effect of promoting hair growth and regrowth.

Experimental Example 5

$2 \times 10^4$ skin keratinocytes (HaCat)/ml were equally seeded into a 24-well plate (SPL, Korea). After 24 hours of stabilization, the keratinocytes were treated for 48 hours with 0.5 µg, 1 µg and 5 µg of the extracellular vesicle-containing filtrate obtained from asparagus in Example 1. MTS reagent (Promega, USA) was diluted with cell basal medium (FBS-free, 1% p/s) at a ratio of 1:5, and 500 µl of the dilution was dispensed into each well of the plate and incubated for 1 hour and 30 minutes. Next, the absorbance at a wavelength of 490 nm was measured to evaluate changes in cell viability, and the results are graphically shown in FIG. 7. In addition, the cell number was counted, and the changes in cell number compared to a control group are graphically shown in FIG. 8. However, the control group was not treated with anything.

Figure 7:
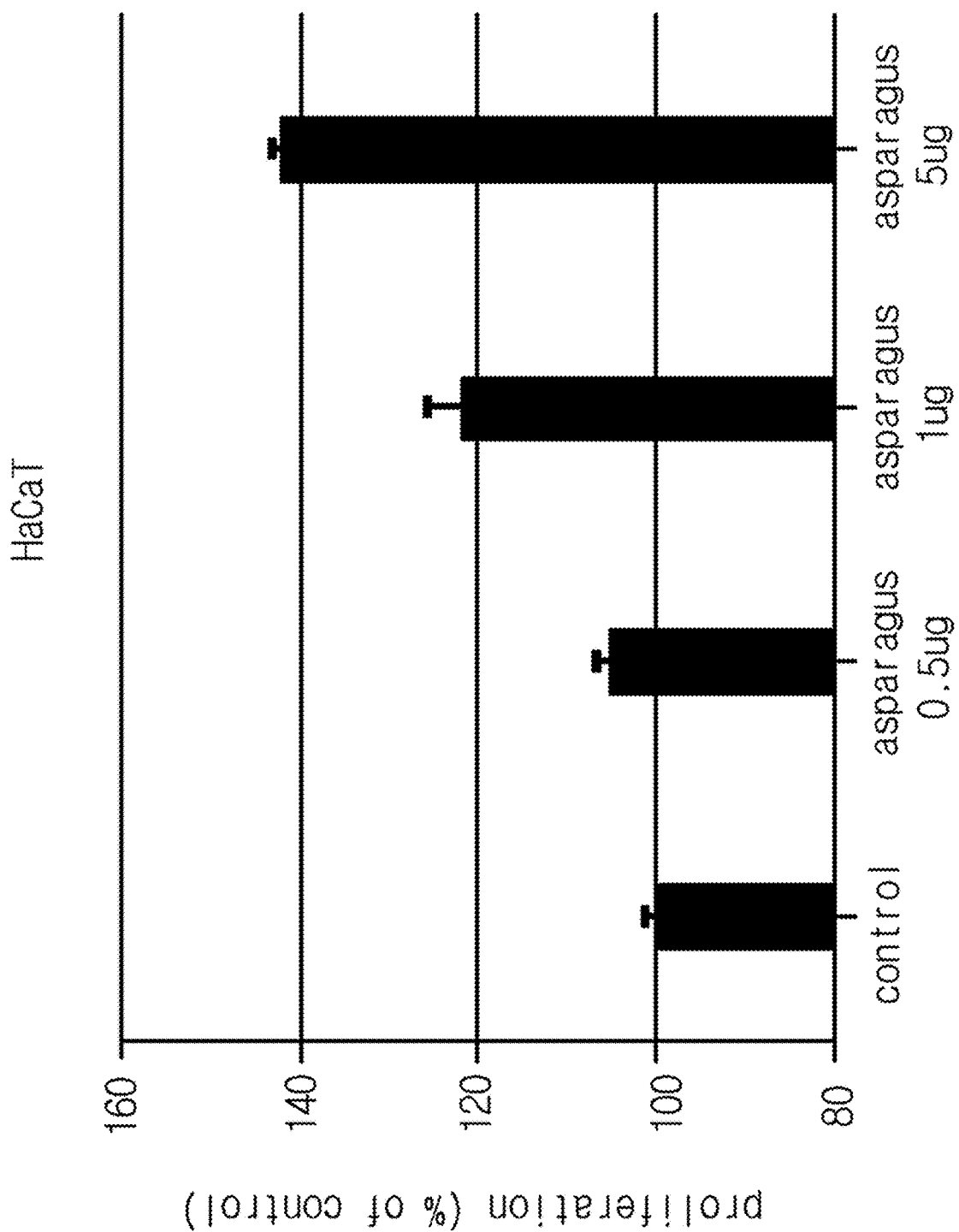
FIG. 7 shows the results of measuring changes in cell viability after treating skin keratinocytes with asparagus-derived extracellular vesicles in Experimental Example 5.
Figure 8:
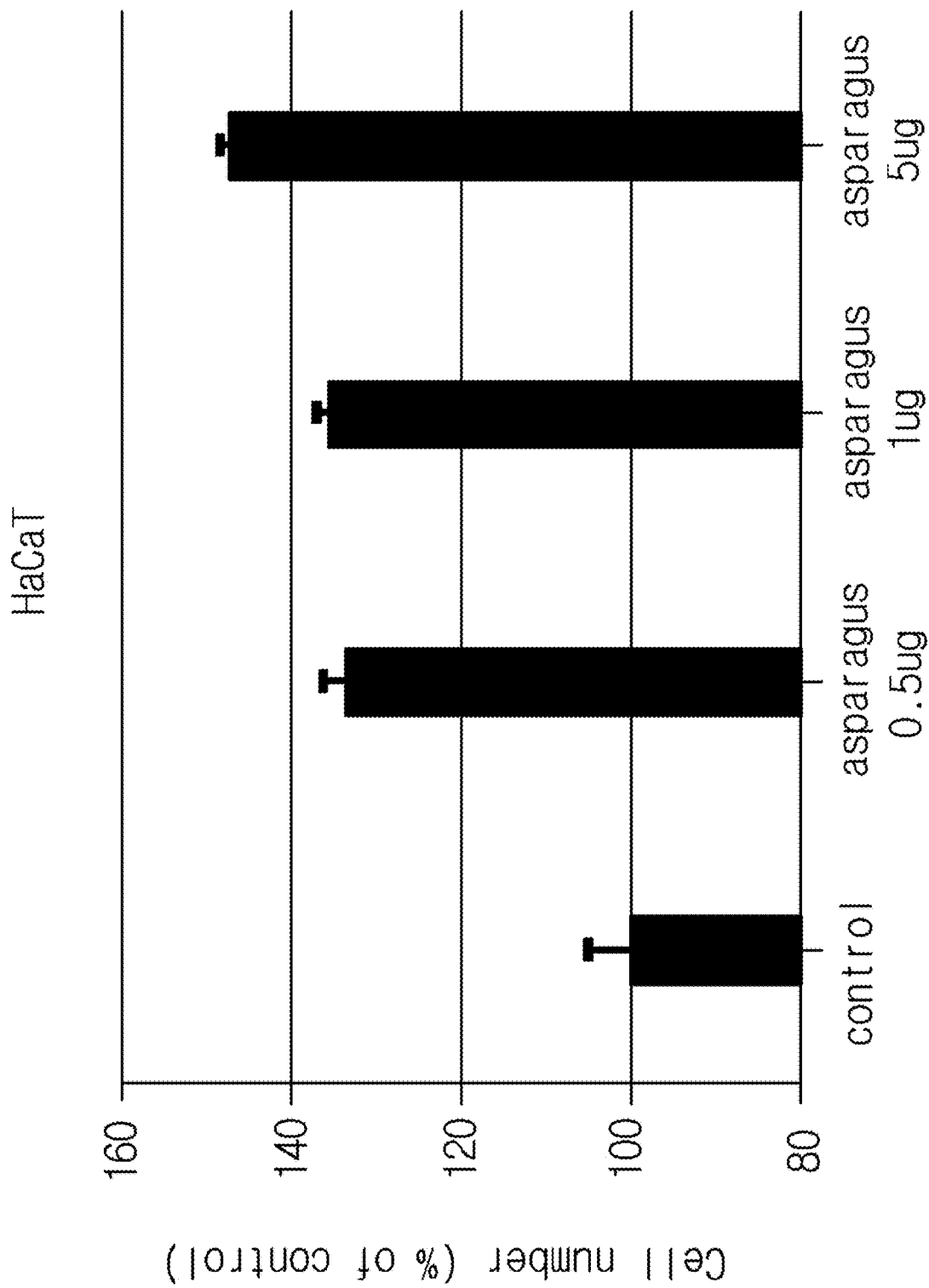
FIG. 8 shows the results of measuring changes in cell number after treating skin keratinocytes with asparagus-derived extracellular vesicles in Experimental Example 5.

As can be seen in FIGS. 7 and 8, when the keratinocytes (HaCat) were treated with the asparagus-derived extracellular vesicles, the proliferation of the keratinocytes increased in a concentration-dependent manner.

Experimental Example 6

Human diploid fibroblasts (HDFs) were attached to a culture dish at a concentration of $5 \times 10^4$ cells/well, and then treated with 5 µg and 10 µg of the extracellular vesicle-containing filtrate obtained from asparagus in Example 1. After 48 hours of culturing, cDNA was synthesized from each cell using an intron premix, and real-time PCR was performed using the cDNA. The expression levels of keratinocyte growth factor, procollagen and basic fibroblast growth factor, which are genes involved in skin aging prevention and skin regeneration, in each treated cell group, were analyzed, and the results are graphically shown in FIGS. 9 to 11.

Figure 9:
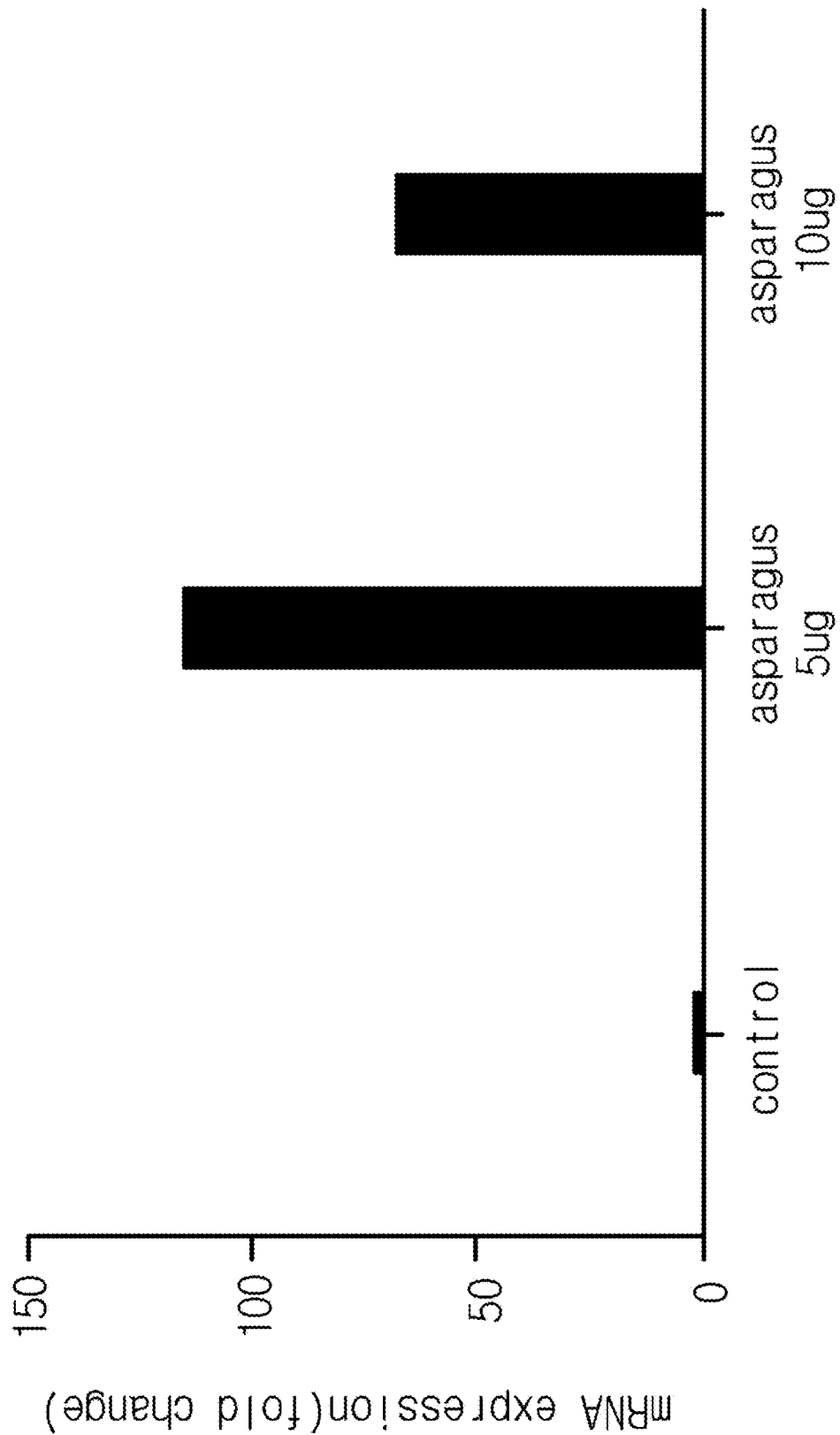
FIG. 9 shows the results of measuring the expression level of keratinocyte growth factor after treating human skin fibroblasts with asparagus-derived extracellular vesicles in Experimental Example 6.
Figure 10:
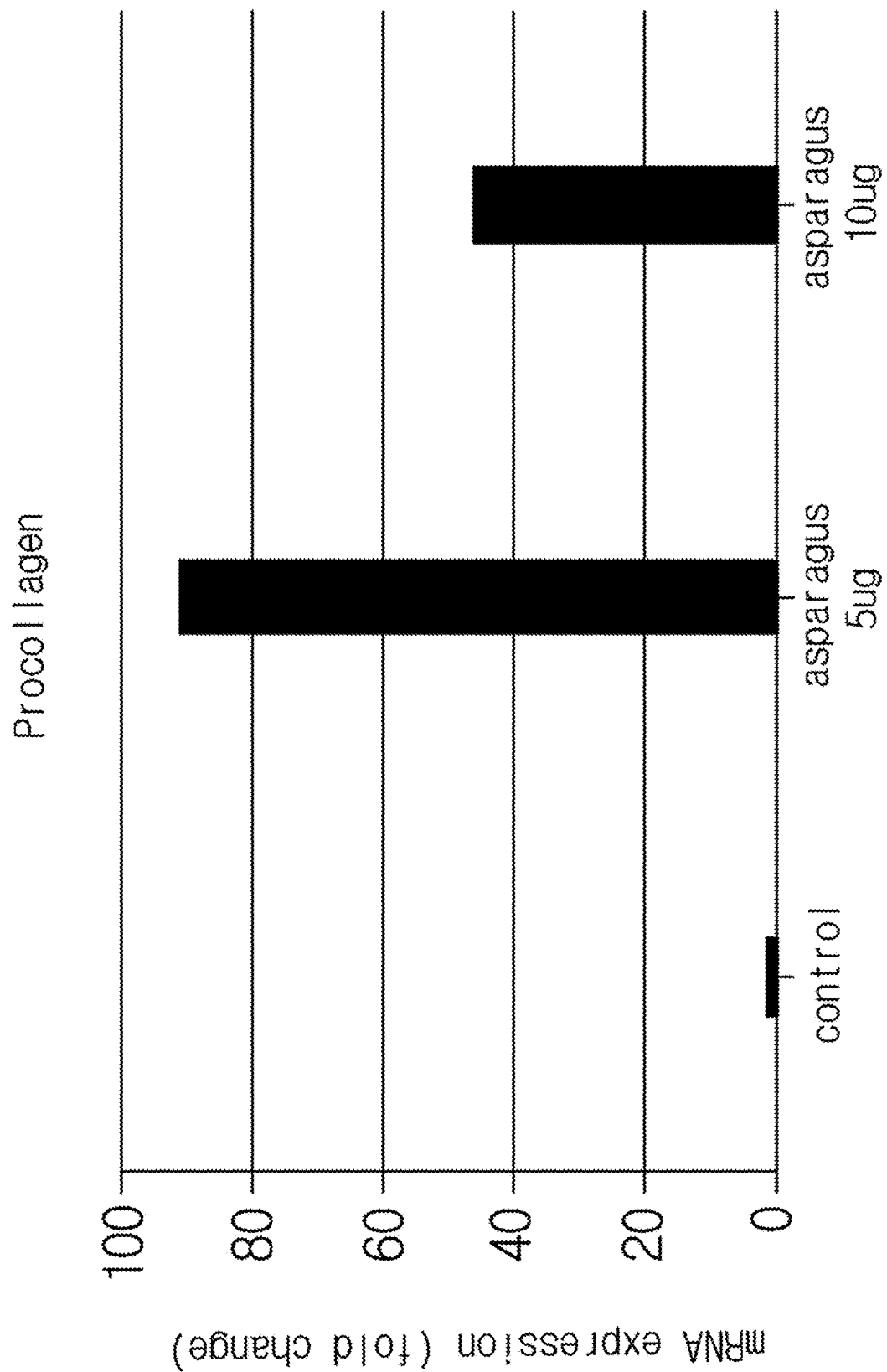
FIG. 10 shows the results of measuring the expression level of procollagen after treating human skin fibroblasts with asparagus-derived extracellular vesicles in Experimental Example 6.
Figure 11:
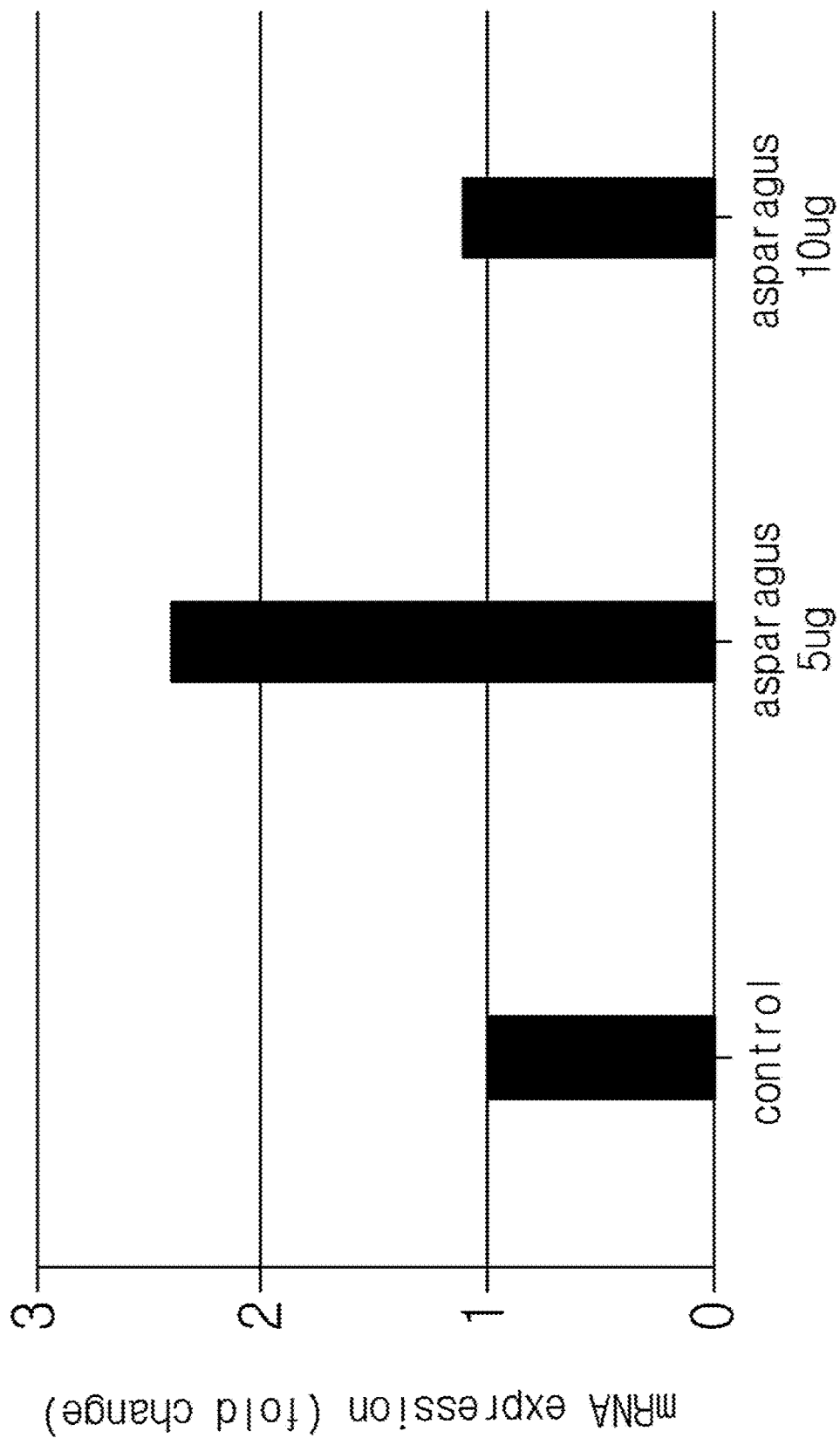
FIG. 11 shows the results of measuring the expression level of fibroblast growth factor after treating human skin fibroblasts with asparagus-derived extracellular vesicles in Experimental Example 6.

As can be seen in FIGS. 9 to 11, when the cells were treated with the asparagus-derived extracellular vesicles, the expression levels of keratinocyte growth factor, procollagen and basic fibroblast growth factor in the cells increased. In particular, it could be seen that when the cells were treated with 5 µg of the asparagus-derived filtrate, the expression levels further increased.

This suggests that the plant-derived extracellular vesicles according to the present invention have an excellent effect on skin aging prevention and skin regeneration and also have an effect on wound healing.

Experimental Example 7

$5 \times 10^4$ melanoma cells (B16F10)/ml were equally seeded into a 6-well plate (SPL, Korea). After 24 hours of stabilization, the cells were treated with 0.5 µg, 1 µg and 5 µg of the extracellular vesicle-containing filtrate obtained from asparagus in Example 1 and 0.5 µg of melanin-inducing a-MSH. After 72 hours of culturing, the supernatant was removed, and the cells were washed once with 2 ml of cold PBS. Next, 550 µl of 1N NaOH was added to each well of the plate to lyse the cells, and then the cells were harvested in a 1.5 ml tube by a pipette, and boiled at 100° C. for 30 minutes, and then centrifuged at 13,000 rpm, and the supernatant was transferred into a fresh tube. 100 µl of the supernatant was transferred into a 96-well plate, after which the change in melanin content compared to the control group was measured by measuring the absorbance at 450 nm, and the results are graphically shown in FIG. 12. However, a positive control group was treated with 0.5 µg of a-MSH alone, and a negative control group was not treated with anything.

Figure 12:
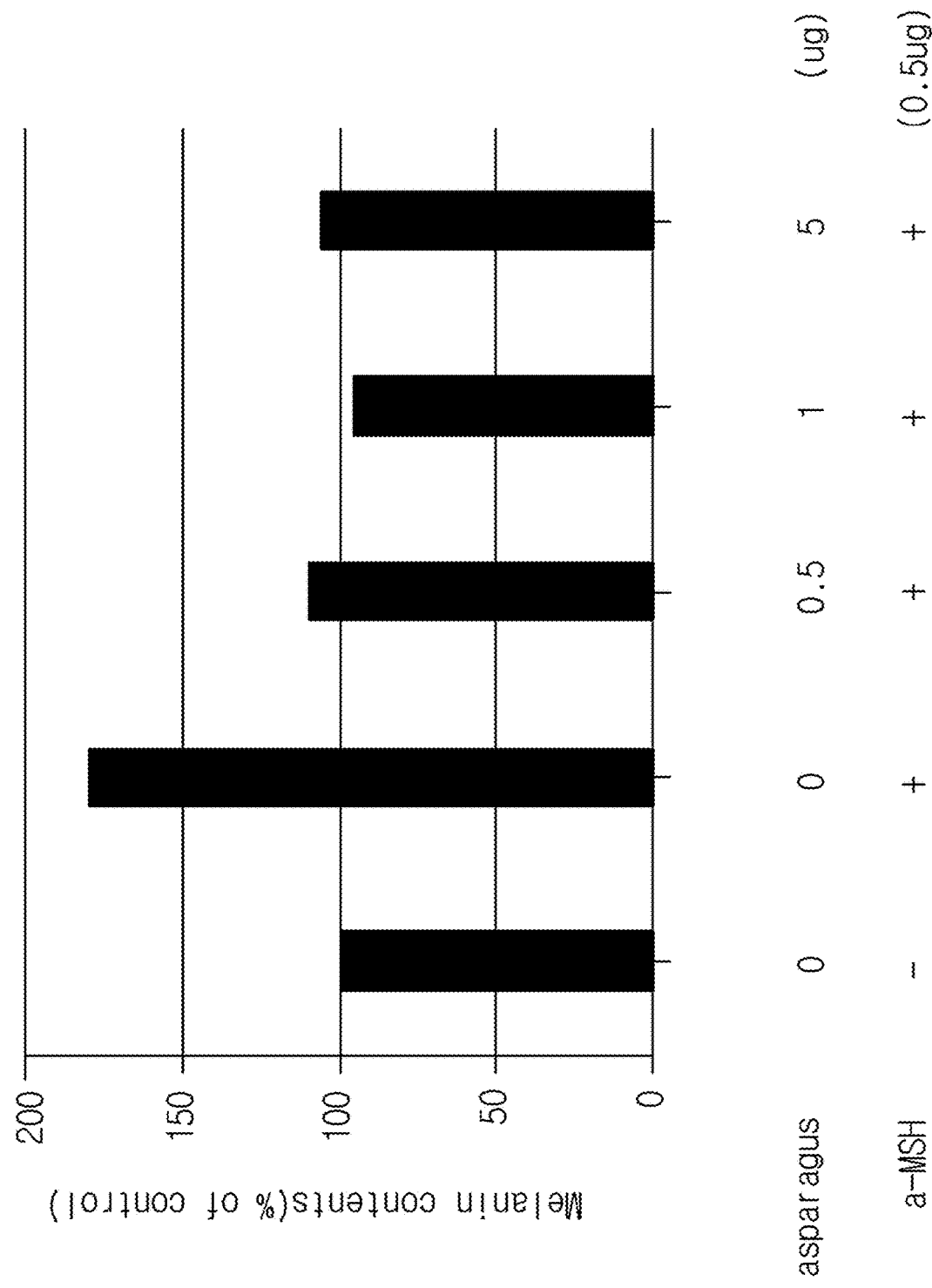
FIG. 12 shows the results of measuring changes in melanin contents after treating melanoma cells with asparagus-derived extracellular vesicles in Experimental Example 7.

As can be seen in FIG. 12, when the cells were treated with the asparagus-derived extracellular vesicles, the melanin content decreased compared to that the control group in which melanin formation was induced with a-MSH.

This suggests that the plant-derived extracellular vesicles according to the present invention have an excellent skin whitening effect.

Experimental Example 8

Cowpea was extracted using a low-speed screw having a stirring speed of 40 rpm, and then centrifuged at 300 g for 10 minutes, 1,200 g for 20 minutes and 10,000 g for 30 minutes to remove large particles. Next, the supernatant was taken and centrifuged using an ultracentrifuge at 100,000 g for 1 hour and 10 minutes, and the precipitated pellets were finally collected, thereby extracting exosomes from cowpea.

Thereafter, dermal papilla cells (DPCs), adipocyte-derived stem cells, human diploid fibroblasts (HDFs) and keratinocytes (HaCaT) were equally seeded into 24-well plates (SPL, Korea) at a concentration of $2 \times 10^4$ cells/ml, respectively. After 24 hours of stabilization, the cells were treated for 48 hours with the cowpea-derived exosomes obtained as described above and the cowpea-derived extracellular vesicles obtained in Example 1. Next, the cell number was counted, and the changes in cell number compared to the control group are graphically shown in FIG. 13. However, the control group was not treated with anything.

Figure 13:
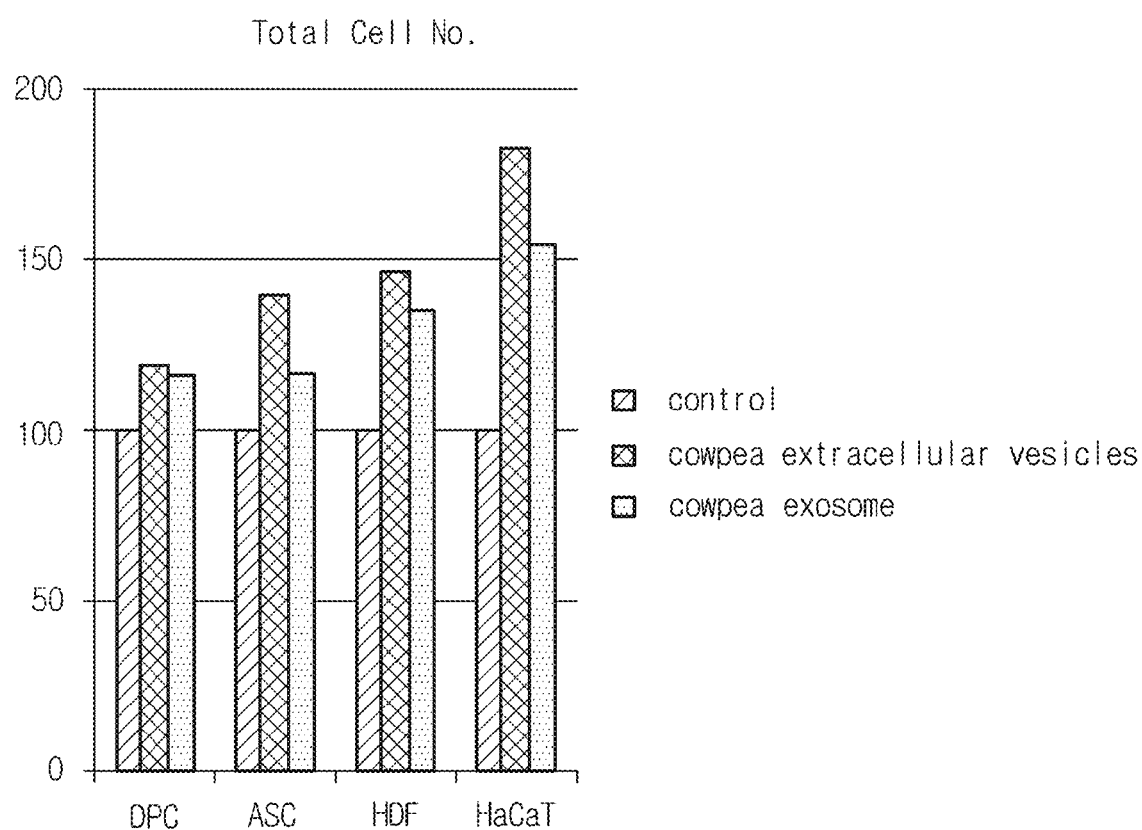
FIG. 13 shows the results of measuring changes in cell number after treating dermal papilla cells, adipocyte-derived stem cells, human skin fibroblasts and keratinocytes with each of cowpea-derived extracellular vesicles and cowpea-derived exosomes in Experimental Example 8.

As can be seen in FIG. 13, the plant-derived extracellular vesicles according to the present invention have a better effect on cell proliferation than the exosomes.

As a result, it can be seen that the plant-derived extracellular vesicles according to the present invention have excellent effects on wound healing, skin condition improvement and hair loss treatment. In addition, extracting the extracellular vesicles according to the present invention from a plant is simpler than the process of extracting exosomes.

Although the present invention has been described with reference to the embodiments, it should be understood that these embodiments are merely illustrative and various modifications and other equivalent embodiments obvious to those skilled in the art may be implemented without departing from the scope of the present invention as defined in the appended claims.

INDUSTRIAL APPLICABILITY

As described above, the use of the extracellular vesicles derived from plant juice according to the present invention can exhibit skin condition-improving effects such as skin whitening, moisturization and wrinkle reduction effects, and prevent hair loss by promotion of hair growth and regrowth, and the like.

The invention claimed is:

1. A method for treating hair loss or promoting hair growth, comprising topically administering to a subject in need thereof a composition comprising as an active ingredient, extracellular vesicles derived from plant juice;
   wherein the plant juice is obtained by extracting a plant using a screw having a stirring speed of 20 to 100 rpm, and
   wherein the plant is cowpea.

2. The method of claim 1, wherein the extracellular vesicles have an average diameter of 100 to 200 nm.

3. A method for treating hair loss or promoting hair growth, comprising topically administering to a subject in need thereof a composition comprising as an active ingredient, extracellular vesicles derived from plant juice;

wherein the plant juice is obtained by extracting a plant using a screw having a stirring speed of 20 to 100 rpm,
wherein the plant is asparagus; and
wherein the extracellular vesicles are contained at a concentration of 5 to 10 µg/ml.

\* \* \* \* \*